(12) United States Patent
Vink et al.

(10) Patent No.: US 9,254,086 B2
(45) Date of Patent: Feb. 9, 2016

(54) WIRELESS DIAGNOSTIC SENSOR LINK

(75) Inventors: Anthony B. Vink, Plymouth Township, MI (US); Michael T. Jewell, Indianapolis, IN (US); Mark P. Zachos, West Bloomfield, MI (US)

(73) Assignee: Dearborn Group, Inc., Farmington Hills, MI (US)

( * ) Notice: Subject to any disclaimer, the term of this patent is extended or adjusted under 35 U.S.C. 154(b) by 163 days.

(21) Appl. No.: 13/314,261

(22) Filed: Dec. 8, 2011

(65) Prior Publication Data
US 2013/0148701 A1 Jun. 13, 2013

(51) Int. Cl.
*H04B 17/00* (2015.01)
*H04W 8/14* (2009.01)
*A61B 5/00* (2006.01)

(52) U.S. Cl.
CPC .................................... *A61B 5/0002* (2013.01)

(58) Field of Classification Search
USPC ............... 455/67.11, 423; 600/445, 590, 300, 600/459, 437, 485
See application file for complete search history.

(56) References Cited

U.S. PATENT DOCUMENTS

| | | | |
|---|---|---|---|
| 6,581,837 B1 * | 6/2003 | Hattersley | 235/462.44 |
| 7,587,388 B2 * | 9/2009 | Auerbach et al. | |
| 2002/0126005 A1 * | 9/2002 | Hardman et al. | 340/442 |
| 2004/0203434 A1 * | 10/2004 | Karschnia et al. | 455/67.11 |
| 2007/0112274 A1 * | 5/2007 | Heitzmann et al. | 600/485 |
| 2008/0039978 A1 * | 2/2008 | Graham | 700/284 |
| 2009/0112072 A1 * | 4/2009 | Banet et al. | 600/301 |

* cited by examiner

*Primary Examiner* — Andrew Wendell
*Assistant Examiner* — Cindy Trandai
(74) *Attorney, Agent, or Firm* — Warn Partners, P.C.

(57) ABSTRACT

A wireless diagnostic sensor link for providing wireless communication between a signal source and a monitoring device. The wireless diagnostic sensor link includes a signal input device operable for receiving a signal from the signal source in a first communication protocol in the form of an analog signal, converting the analog signal to a digital signal, and transmitting the digital signal in the form of a wireless communication protocol. The wireless diagnostic sensor link also includes a signal output device, which receives the digital signal. The signal output device is in electrical communication with the monitoring device, and is also operable for communicating with the signal input device. The signal output device converts the digital signal back to an analog signal, and sends the signal to the monitoring device in the form of a second communications protocol.

17 Claims, 2 Drawing Sheets

WIRELESS DIAGNOSTIC SENSOR LINK

FIELD OF THE INVENTION

The present invention relates to a wireless diagnostic sensor link for providing wireless communication between a signal source, such as a transducer kit, and a monitoring device, such as a protocol adapter or a computer.

BACKGROUND OF THE INVENTION

A transducer is a device that converts one type of energy to another. The conversion can be to/from electrical, electromechanical, electromagnetic, photonic, photovoltaic, or any other form of energy. While the term "transducer" commonly implies use as a sensor/detector, any device which converts energy can be considered a transducer. A transducer, or transducer kit (TK), is often categorized by application: sensor, actuator, or combination.

A transducer in the form of a sensor is used to detect a parameter in one form and report it in another form of energy (usually an electrical and/or digital signal). For example, a pressure sensor might detect pressure (a mechanical form of energy) and convert it to electricity for display at a remote gauge.

A transducer in the form of an actuator accepts energy and produces movement (action). The energy supplied to an actuator might be electrical or mechanical (pneumatic, hydraulic, etc.). An electric motor and a loudspeaker are both transducers, converting electrical energy into motion for different purposes.

Combination transducers have both functions—they both detect and create action. For example, a typical ultrasonic transducer switches back and forth many times a second between acting as an actuator to produce ultrasonic waves, and acting as a sensor to detect ultrasonic waves.

Modern TK devices are interfaced with a personal computer through the use of a cable connection, such as a Universal Serial Bus (USB), or the like. The interface allows the computer to record measurements as they are made if the transducer is functioning as a sensor, or send commands to the transducer, if the transducer is functioning as an actuator.

However, using an actual wire connection between a TK and a computer, such as a USB or the like, is limiting because the TK and device under test must be located at a distance in relation to the computer. The distance between the TK and device under test must be substantially equal to or less than the length of the wire because the wire must be connected to both the computer and the transducer. This limits the use of a TK when it is physically impossible to have the device under test in proximity to the computer such that the wire connection can be made between the TK and the computer.

Several attempts have been made to provide a wireless connection between a transducer or other diagnostic sensor, and a device such as a computer or protocol adapter. Many of these attempts have involved converting a first communications protocol in the form of an analog signal to a digital signal, then converting the digital signal to a wireless communications protocol, such as an RF or infrared signal, and transmitting the signal wirelessly from the transducer or other diagnostic sensor to the protocol adapter or computer, then performing another protocol conversion to convert the signal from a wireless signal back to a digital signal suitable for use with the communication protocol used by the protocol adapter or computer. However, this process involves several protocol conversions, such as analog-to-digital and digital-to-analog, and wireless to digital. Additionally, the upper frequency end of messages or sensor signals is restricted, and because there are at least two adapters for performing the analog-to-digital and digital-to-analog conversions, the device or system has an increased number of components.

Accordingly, there exists a need for a device such as a TK which is able to record desired measurements or parameters of a device under test, and communicate wirelessly with a computer, allowing the computer to record the measurements or parameters, without limiting the location of the computer or the device under test, while limiting the amount of conversions of the signal from the TK.

SUMMARY OF THE INVENTION

The present invention is a wireless diagnostic sensor link for providing wireless communication between a signal source and a monitoring device. The wireless diagnostic sensor link includes a signal input device operable for receiving a signal from the signal source in the form of an analog signal, converting the analog signal to a digital signal, and transmitting the digital signal wirelessly. The wireless diagnostic sensor link also includes a signal output device, which receives the digital signal. The signal output device is in electrical communication with the monitoring device, and is also operable for communicating with the signal input device. The signal output device converts the digital signal back to an analog signal, and sends the signal to the monitoring device.

In one embodiment, the signal source is a transducer which records a voltage signal, and sends a wireless "snap shot" of the signal's voltage levels to a device such as a protocol adapter or computer. This wireless transmission is accomplished by a radio transmitter. The wireless diagnostic sensor link provides a wireless pass-through of one or more signals from a connection or tap in the path of the electrical signal to a remote monitoring device, such as a protocol adapter or computer, without conversion of the raw data.

The radio transmitter is able to broadcast in one or more wireless communication protocols. The wireless communication protocols include, but are not limited to, Zigbee, Wifi, infrared, Infrared Data Association (IrDA), Bluetooth, Ultra-wideband (UWA), and Z-Wave.

The wireless diagnostic sensor link of the present invention is suitable for operation with any type of transducer that functions as a sensor/detector, an actuator, or the like, and is able to transfer the data detected by the transducer wirelessly to a computer.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
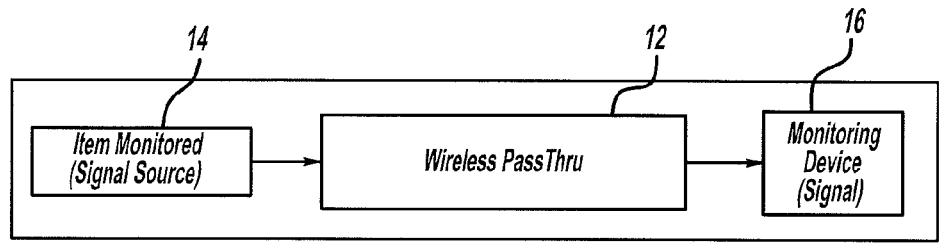
FIG. 1 is a block diagram showing the basic operation of a wireless diagnostic sensor link, according to the present invention.

A block diagram for a wireless diagnostic sensor link is shown in FIG. 1 generally at 10. The wireless diagnostic sensor link 12 according to the present invention is used for providing communication between a signal source 14, such as a transducer kit (TK), and a monitoring device 16, such as a protocol adapter or laptop/desktop computer.

Figure 2:
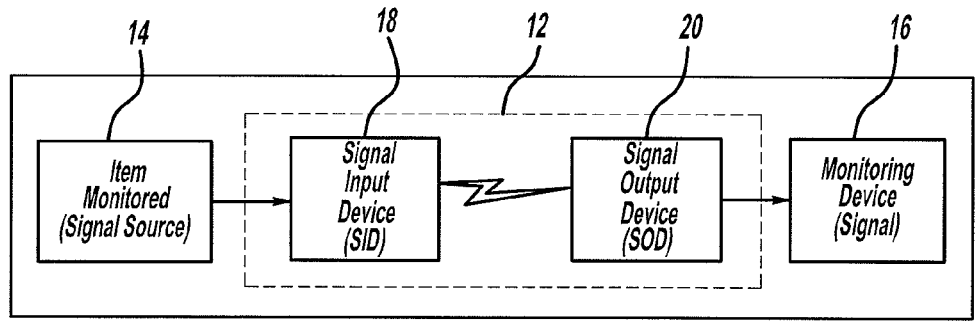
FIG. 2 is a block diagram of the physical operation of a wireless diagnostic sensor link, according to the present invention.

Referring to FIG. 2, the wireless diagnostic sensor link 12 includes a signal input device 18 in wireless communication with a signal output device 20. The signal input device 18 is in electrical communication with the signal source 14, and the signal output device 20 is in electrical communication with the monitoring device 16.

Figure 3:
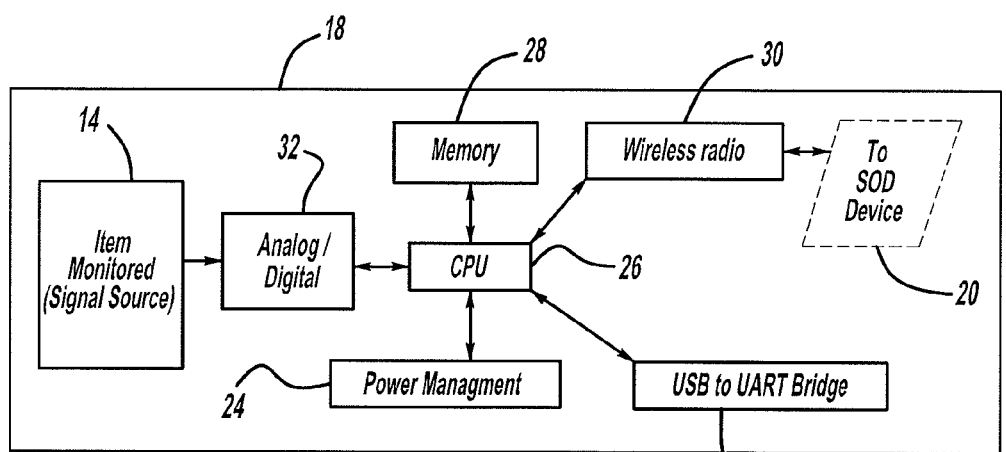
FIG. 3 is a block diagram of a signal input device used as part of a wireless diagnostic sensor link, according to the present invention.

Referring to FIG. 3, a block diagram having more detail of the signal input device 18 is shown. The signal input device 18 is also connectable to a charging device through the use of a Universal Serial Bus (USB) connector (not shown), that is connected to a USB to Universal Asynchronous Receive/Transmit (UART) Bridge 22 which is in electrical communication with a power management system 24 through a processor 26. The power management system 24 includes a battery manager/charger in electrical communication with the USB connector, a power source, such as a battery, and a power activation switch. When the USB connector is connected to a charging device, the manager/charger is operable to control and direct charge to the battery. The battery used in the power management system 24 of the present invention is a lithium-ion battery which is able to retain charge for thirty days when not in use (stand-by mode), and is capable of four hours of continuous operation when in use (active mode).

The battery manager/charger is also in electrical communication with the power activation switch, and the power activation switch and the battery manager/charger are in electrical communication with the processor 26. In this embodiment, the processor is a 32-bit Advanced RISC Machine (ARM) processor 26. The processor 26 has at least one memory device 28, which in this embodiment has both flash memory as well as Static Random Access Memory (SRAM), although it is within the scope of the invention that other types of memory may be used. The processor 26 is in electrical communication with the USB to UART Bridge 22. The processor 26 is also in electrical communication with at least one radio transmitter 30. In this embodiment, there is one radio transmitter, but it is within the scope of the invention that more than one radio transmitter may be used for providing wireless communication. The transmitter 30 has the capability to transmit in both Zigbee and WiFi communication protocols. The USB to UART Bridge 22 is in electrical communication with the USB connector by way of a data communication line.

The processor 26 is in electrical communication with a connector, such as, but not limited to, a multiple pin connector, and the multiple pin connector is connected to the signal source 14. In an alternate embodiment, a signal conditioner is positioned and placed in electrical communication between the multiple pin connector and the processor 26, which conditions the signal between the multiple pin connector and the processor 26. The signal conditioning performed by the signal conditioner may include amplification, filtering, range matching, isolation, or any other process desired by the user. There is also a first analog-to-digital (A/D) converter 32 in electrical communication with the signal source 14, and the A/D converter 32 is also in electrical communication with the processor 26.

In one embodiment, the signal source 14 is a transducer kit connected to the multiple pin connector. When the TK measures a desired parameter in terms of a voltage, a reference voltage, which is very precise, is used as a reference to determine the magnitude of the measurement.

Figure 4:
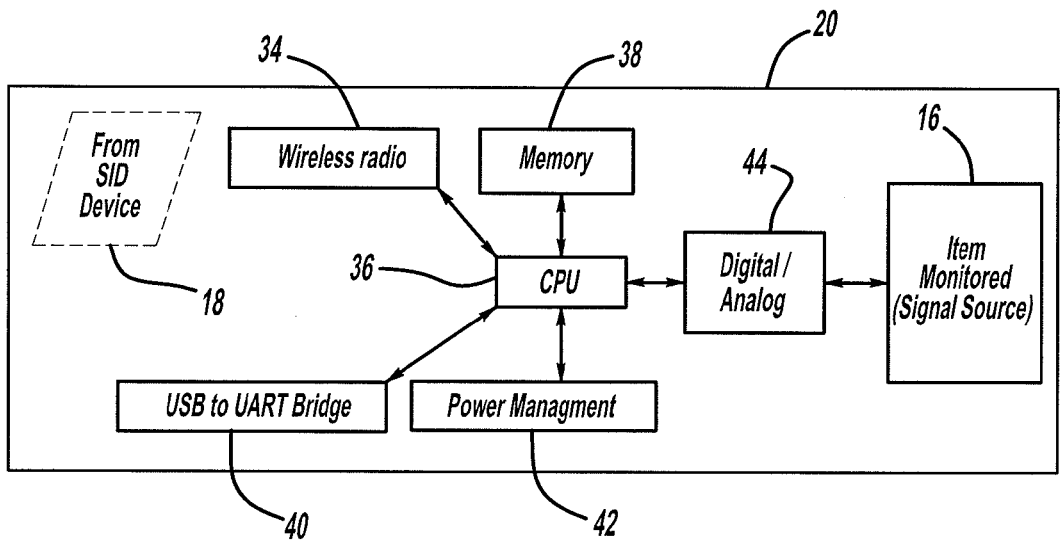
FIG. 4 is a block diagram of a signal output device used as part of a wireless diagnostic sensor link, according to the present invention.

Referring now to FIG. 4, a block diagram having more detail of the signal output device 20 is shown. The signal output device 20 has similar components to the signal input device 18. There is a radio transmitter 34 which is in electrical communication with a second processor 36, and the second processor 36 has a second memory device 38 similar to the first memory device 28, and includes both flash memory and SRAM. The processor 36 is also in electrical communication with a second USB to UART Bridge 40, which is similar to the first USB to UART Bridge 22. The second USB to UART Bridge 40 is also in electrical communication with a second USB connector (not shown) by a data communication line, and the second USB connector performs the same functions as the USB connector of the signal input device 18.

Also in electrical communication with the processor 36 is a second power management system 42 which is similar to the first power management system 24. The second power management system 42 has a battery manager/charger in electrical communication with the second USB connector, a battery, and a power activation switch. The second USB connector of the signal output device 20 is also able to be connected to a charging device, and the battery charger/manager. A second A/D converter 44 is in electrical communication with the processor 36 and is also in electrical communication with the monitoring device 16.

In operation, the signal input device 18 is in a dormant or inactive state when not in use, where minimal power is used from the power management system 24 such that the multiple pin connector is able to detect a signal received from signal source 14. The power management system 24 interacts with the multiple pin connector in such a manner that if a signal is sent to the multiple pin connector, the signal is detected by the power management system 24, and the power activation switch of the power management system 24 activates the processor 26, thereby activating the signal input device 18. In one embodiment, the signal source 14 for use with the sensor link 12 of the present invention is a commercial, off the shelf TK. The processor 26 then begins to communicate with the TK through the A/D converter 32. The A/D converter 32 receives a signal from the TK in the form of an analog signal. The A/D converter 32 converts the signal from an analog signal to a digital signal. As the signal input device 18 receives signals from the TK, the processor 26 sends the signal to the radio transmitter 30, where the radio transmitter 30 broadcasts the digital signal wirelessly.

Once the radio transmitter 30 receives the signals from the processor 26 and the transmitter 30 broadcasts the digital signal wirelessly, the second radio transmitter 34 receives the signal. While the transmitters 30,34 used with the signal input device 18 and signal output device 20 of the present invention broadcast in either Zigbee or WiFi wireless communication protocols, it is within the scope of the invention that other wireless communication protocols may be used. Other wireless communication protocols include, but are not limited to, Infrared Data Association (IrDA), Bluetooth, Ultra-wideband (UWA), and Z-Wave. Additionally, the transmitters 30,34 are also operable to communicate in different wireless communication protocols. The respective processors 26,36 then receive the various signals and are able to process the data received as desired by the user.

Once the second radio transmitter 34 receives the signal, the signal is sent to the second processor 36, the second processor 36 then sends the signal to the second A/D converter 44, where the signal is then converted from a digital signal back to an analog signal (i.e., converted to a second analog signal), and is then sent to the monitoring device 16, where the signal is stored, processed, or evaluated as desired. If the signal output device 20 is in a dormant or inactive state when the second radio transmitter 34 receives a signal from the first radio transmitter 30, the signal is detected by the second power management system 42 such that the second power activation switch of the second power management system 42 activates the second processor 36, thereby activating the signal output device 20.

The wireless transmission of the signal may be in the form of a "snap shot" of the signal's voltage levels that is sent from the signal input device 18 to the signal output device 20. For example, it may not be necessary to continuously stream data from the signal input device 18, but rather a sample or data point may be taken at predetermined intervals, such as once per second, or once every three-hundred milliseconds, or any other time interval desired. The data collected during the "snap shot" is then sent to the signal output device 20. In an alternate embodiment, the signal may be streamed to the signal output device 20 from the signal input device 18, depending on which wireless communication protocol is used.

As mentioned above, in one embodiment, the signal source 14 is a TK capable of measuring various types of parameters, such as current, voltage, resistance, or the like, for measuring a desired parameter, such as, but not limited to temperature, pressure, or force. The data for the parameter measured by the TK is transferred to the signal input device 18 through the multiple pin connector. The transmission of data between the signal input device 14 and the signal output device 18 is wireless because of the radio transmitters 30,34, and occurs without the conversion of raw data. It should be noted that the wireless diagnostic sensor link 12 may be used for many different types of applications. In one embodiment, the TK is used for measuring a parameter during the operation of a vehicle, and the wireless diagnostic sensor link 12 provides communication between the TK and the monitoring device. In other embodiments, the TK may be used on an oil rig platform, a seismology test site, a wind power generate site, a solar panel power field, or any other application requiring the recording of a sensed parameter, where a monitoring device, such as a computer or protocol adapter, is at a remote location relative to the TK such that a wireless communication between the monitoring device and TK is required.

Figure 5:
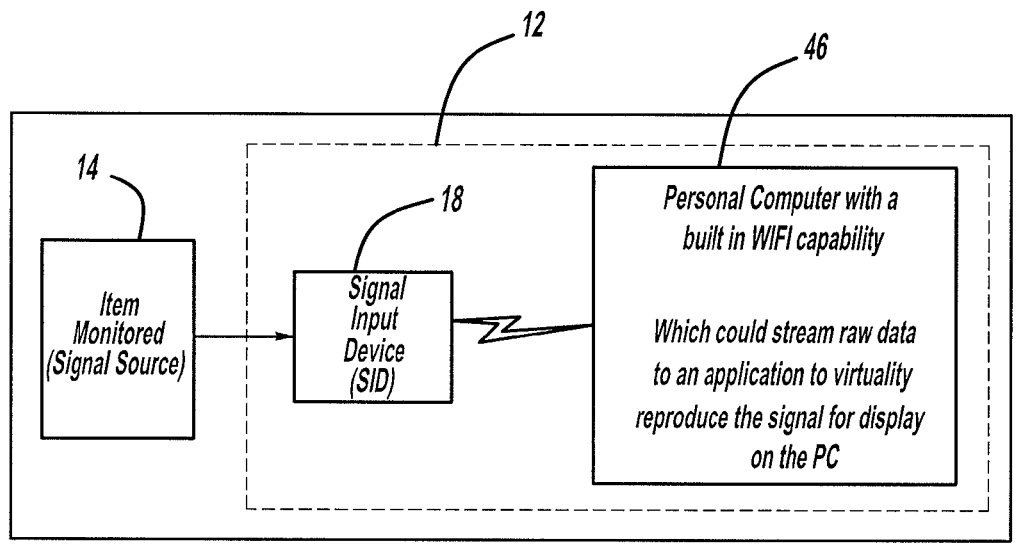
FIG. 5 is a block diagram of an alternate embodiment of a wireless diagnostic sensor link, according to the present invention.

An alternate embodiment of the sensor link 12 according to the present invention is shown in FIG. 5, where like numbers refer to like elements. In this embodiment, instead of having the signal output device 20, the sensor link 12 has a WiFi capable device 46. The WiFi capable device 46 may be any type of device with WiFi capability, such as a laptop computer, a smart phone, or the like. In this embodiment, the device 46 streams raw data to an application to virtually reproduce the signal received from the signal input device 18 for display. The device 46 is able to accumulate the data received from the signal input device 18 such that the data is able to be displayed at a later time, such that moment to moment monitoring (or replication of the electrical signal) is not a factor.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A wireless diagnostic sensor link for providing wireless communication of raw data between a signal source and a monitoring device, comprising:
    said signal source is a transducer kit that measures a desired parameter during an operation of a vehicle in terms of a measured voltage and further including a reference voltage used by the transducer kit to determine the magnitude of the measured voltage;
    a signal input device having a first processor and a first analog-to-digital converter in electrical communication with said first processor, said first analog-to-digital converter is configured to receive an analog signal from said signal source and convert said analog signal to a digital signal in at least one wireless communication protocol, such that said first processor receives said digital signal from said first analog-to-digital converter;
    a power management system of the signal input device;
    a multiple pin connector connected between the signal source and the signal input device, wherein the signal input device is in a dormant state when not in use, where minimal power is used by the power management system such that the multiple pin connector is able to detect a signal received from the signal source and the power management system and a power activation switch of the power management system activates the first processor, thereby activating the signal input device;
    a first radio transmitter of said signal input device in electrical communication with said first processor, said first processor transmits said digital signal to said first radio transmitter;
    a signal output device having a second radio transmitter in wireless communication with said first radio transmitter in said at least one wireless communication protocol, wherein said first radio transmitter wirelessly transmits said digital signal to the signal output device in said at least one wireless communication protocol, wherein said digital signal transmitted by said first radio transmitter is a snapshot sample data point;
    a second processor of said signal output device in electrical communication with said second radio transmitter such that said second processor receives said digital signal from said second radio transmitter; and
    a second analog-to-digital converter of said signal output device in electrical communication with said second processor, said second analog-to-digital converter operable for receiving said digital signal from said second processor, and converting said digital signal to a second analog signal prior to sending said second analog signal to said monitoring device.

2. The wireless diagnostic sensor link for providing wireless communication between the signal source and the monitoring device of claim 1, said at least one wireless communication protocol being one selected from a group consisting of Zigbee, Wifi, infrared, Infrared Data Association (IrDA), Bluetooth, Ultra-wideband (UWA), and Z-Wave.

3. The wireless diagnostic sensor link for providing wireless communication between the signal source and the monitoring device of claim 1, said signal source further comprising a transducer.

4. The wireless diagnostic sensor link for providing wireless communication between the signal source and the monitoring device of claim 3, wherein said transducer measures the parameter that is one selected from a group consisting of temperature, pressure, force, and combinations thereof.

5. The wireless diagnostic sensor link for providing wireless communication between the signal source and the monitoring device of claim 1, said monitoring device being one selected from a group consisting of a protocol adapter and a computer.

6. The wireless diagnostic sensor link for providing wireless communication between the signal source and the monitoring device of claim 1, wherein said signal source measures the parameter at predetermined time intervals, and transmits said measured parameter to said signal input device.

7. A wireless diagnostic sensor link for providing wireless communication of raw data between a signal source and a monitoring device, comprising:
the signal source for producing a first analog signal, wherein the signal source is a transducer kit that measures a desired parameter during an operation of a vehicle in terms of a measured voltage and further including a reference voltage used by the transducer kit to determine the magnitude of the measured voltage;
a signal input device having a first processor and a first analog-to-digital converter in electrical communication with said first processor, said first analog-to-digital converter is configured to receive said first analog signal from said signal source and convert said first analog signal to a digital signal in at least one wireless communication protocol, such that said first processor receives said digital signal from said first analog-to-digital converter;
a power management system of the signal input device;
a multiple pin connector connected between the signal source and the signal input device, wherein the signal input device is in a dormant state when not in use where minimal power is used by the power management system such that the multiple pin connector is able to detect a signal received from the signal source and the power management system and a power activation switch of the power management system activates the first processor, thereby activating the signal input device;
a first radio transmitter of said signal input device in electrical communication with said first processor, said first processor transmits said digital signal to said first radio transmitter, wherein said digital signal transmitted by said first radio transmitter is a snapshot sample data point;
a signal output device having a second radio transmitter in wireless communication with said first radio transmitter in said at least one wireless communication protocol, wherein said first radio transmitter wirelessly transmits said digital signal to the signal output device in said at least one wireless communication protocol;
a second processor of said signal output device in electrical communication with said second radio transmitter such that said second processor receives said digital signal from said second radio transmitter; and
a second analog-to-digital converter of said signal output device in electrical communication with said second processor, said second analog-to-digital converter operable for receiving said digital signal from said second processor, and converting said digital signal to a second analog signal prior to sending said second analog signal to said monitoring device; and
a monitoring device in electrical communication with said second analog-to-digital converter such that said monitoring device receives said second analog signal from said second analog-to-digital converter.

8. The wireless diagnostic sensor link for providing wireless communication between the signal source and the monitoring device of claim 7, said at least one wireless communication protocol being one selected from a group consisting of Zigbee, Wifi, infrared, Infrared Data Association (IrDA), Bluetooth, Ultra-wideband (UWA), and Z-Wave.

9. The wireless diagnostic sensor link for providing wireless communication between the signal source and the monitoring device of claim 7, wherein said signal source measures the parameter at predetermined time intervals, and transmits said measured parameter to said signal input device.

10. The wireless diagnostic sensor link for providing wireless communication between the signal source and the monitoring device of claim 7, said monitoring device being one selected from a group consisting of a protocol adapter and a computer.

11. The wireless diagnostic sensor link for providing wireless communication between the signal source and the monitoring device of claim 7, said signal source further comprising a transducer.

12. The wireless diagnostic sensor link for providing wireless communication between the signal source and the monitoring device of claim 11, wherein said transducer measures the parameter that is one selected from a group consisting of temperature, pressure, force, and combinations thereof.

13. A wireless diagnostic sensor link for providing wireless communication of raw data between a signal source and a monitoring device, comprising:
the signal source is a transducer kit that measures a desired parameter during an operation of a vehicle in terms of a measured voltage and further including a reference voltage used by the transducer kit to determine the magnitude of the measured voltage;
a first analog-to-digital converter for receiving a first analog signal from said signal source, and converting said first analog signal to a digital signal in at least one wireless communication protocol;
a first processor in electrical communication with said first analog-to-digital converter, and operable for receiving said digital signal from said first analog-to-digital converter;
a first radio transmitter in electrical communication with said first processor such that said first radio transmitter receives said digital signal and wirelessly transmits said digital signal in said at least one wireless communication protocol, wherein said digital signal transmitted by said first radio transmitter is a snapshot sample data point;
a power management system electrically connected to the first analog-to-digital converter, said first processor and said first radio transmitter;
a multiple pin connector connected between the signal source and the first analog-to-digital device, wherein the first analog-to-digital converter, said first processor and said first radio transmitter are in a dormant state when not in use and minimal power is used by the power management system such that the multiple pin connector is able to detect a signal received from the signal source and the power management system and a power activation switch of the power management system activates the first processor, thereby activating the signal input device;

a second radio transmitter in wireless communication with said first radio transmitter in said at least one wireless communication protocol such that said second radio transmitter receives said digital signal from said first radio transmitter;

a second processor in electrical communication with said second radio transmitter, said second processor receives said digital signal from said second radio transmitter;

a second analog-to-digital converter in electrical communication with said second processor such that said second analog-to-digital converter receives said digital signal from said second radio transmitter in said at least one wireless communication protocol, and converts said digital signal to a second analog signal and sends said second analog signal to said second processor; and the monitoring device operable for receiving said second analog signal from said second analog-to-digital converter.

14. The wireless diagnostic sensor link for providing wireless communication between the signal source and the monitoring device of claim 13, said monitoring device further comprising a transducer operable for measuring the parameter that is one selected from a group consisting of temperature, pressure, force, and combinations thereof.

15. The wireless diagnostic sensor link for providing wireless communication between the signal source and the monitoring device of claim 13, said at least one wireless communication protocol being one selected from a group consisting of Zigbee, Wifi, infrared, Infrared Data Association (IrDA), Bluetooth, Ultra-wideband (UWA), and Z-Wave.

16. The wireless diagnostic sensor link for providing wireless communication between the signal source and the monitoring device of claim 13, wherein said signal source measures the parameter at predetermined time intervals, and transmits said measured parameter to said signal input device.

17. The wireless diagnostic sensor link for providing wireless communication between the signal source and the monitoring device of claim 13, said monitoring device being one selected from a group consisting of a protocol adapter and a computer.

* * * * *